United States Patent
Harding

(10) Patent No.: US 10,130,319 B2
(45) Date of Patent: Nov. 20, 2018

(54) RADIATION IMAGING

(71) Applicant: FLEXENABLE LIMITED, Cambridge (GB)

(72) Inventor: Matthew James Harding, Cambridge (GB)

(73) Assignee: FLEXENABLE LIMITED, Cambridge (GB)

( * ) Notice: Subject to any disclaimer, the term of this patent is extended or adjusted under 35 U.S.C. 154(b) by 214 days.

(21) Appl. No.: 14/902,870

(22) PCT Filed: Jul. 2, 2014

(86) PCT No.: PCT/EP2014/064121
§ 371 (c)(1),
(2) Date: Jan. 5, 2016

(87) PCT Pub. No.: WO2015/003981
PCT Pub. Date: Jan. 15, 2015

(65) Prior Publication Data
US 2016/0183895 A1  Jun. 30, 2016

(30) Foreign Application Priority Data
Jul. 8, 2013 (GB) .................................. 1312208.8

(51) Int. Cl.
| A61B 6/00 | (2006.01) |
| G01T 1/00 | (2006.01) |
| G01T 1/24 | (2006.01) |
| G01T 1/20 | (2006.01) |

(52) U.S. Cl.
CPC ............. *A61B 6/461* (2013.01); *G01T 1/20* (2013.01); *G01T 1/24* (2013.01); *G01T 1/242* (2013.01)

(58) Field of Classification Search
CPC .............................. A61B 6/461; G01T 1/242
See application file for complete search history.

(56) References Cited

U.S. PATENT DOCUMENTS 5,847,499 A   12/1998  Rieppo et al.

FOREIGN PATENT DOCUMENTS

| EP | 0 574 690 A2 | 12/1993 |
| WO | 2010/120296 A1 | 10/2010 |
| WO | 2012/034229 A1 | 3/2012 |
| WO | 2012/057759 A1 | 5/2012 |

OTHER PUBLICATIONS

International Search Report for PCT/EP2014/064121 dated Aug. 26, 2014.
Written Opinion for PCT/EP2014/064121 dated Aug. 26, 2014.

*Primary Examiner* — Dani Fox
(74) *Attorney, Agent, or Firm* — Sughrue Mion, PLLC

(57) ABSTRACT

A device, comprising: a display component; and a drive component comprising a stack of layers defining an array of display pixel conductors each connected within the stack of layers to a drive conductor by a respective radiation-sensitive channel, wherein a change in the intensity of radiation to which a radiation-sensitive channel is exposed causes a change in the electric potential at the respective display pixel conductor relative to a drive voltage applied to the drive conductor and the change in the electric potential at the respective display pixel conductor causes a change in the display of the respective pixel area of the display component.

20 Claims, 3 Drawing Sheets

RADIATION IMAGING

CROSS REFERENCE TO RELATED APPLICATIONS

This application is a National Stage of International Application No. PCT/EP2014/064121 filed Jul. 2, 2014, claiming priority based on British Patent Application No. 1312208.8 filed Jul. 8, 2013, the contents of all of which are incorporated herein by reference in their entirety.

A conventional technique for imaging radiation involves processing the output of a pixelated sensing device, and then displaying the result of the processing in the form of an image on a display device.

The inventors for the present invention have developed an alternative approach to radiation imaging.

There is hereby provided a device, comprising: a display component; and a drive component comprising an array of pixel conductors each connected to a drive conductor by a respective radiation-sensitive channel, wherein a change in the intensity of radiation to which a radiation-sensitive channel is exposed causes a change in the electric potential at the respective pixel conductor relative to a drive voltage applied to the drive conductor and a change in the display of the respective pixel area of the display component.

There is hereby provided a device, comprising: a display component; and a drive component comprising a stack of layers defining an array of display pixel conductors each connected within the stack of layers to a drive conductor by a respective radiation-sensitive channel, wherein a change in the intensity of radiation to which a radiation-sensitive channel is exposed causes a change in the electric potential at the respective display pixel conductor relative to a drive voltage applied to the drive conductor, and the change in the electric potential at the respective display pixel conductor causes a change in the display of the respective pixel area of the display component.

According to one embodiment, the radiation is visible light.

According to one embodiment, the device further comprises: a scintillator comprising a portion in the region of each radiation-sensitive channel, wherein respective portions of the scintillator generate a first type of radiation in the region of respective ones of the radiation-sensitive channels upon exposure to a second, different type of radiation.

According to one embodiment, said first type of radiation is visible light and/or ultraviolet radiation.

According to one embodiment, said second, different type of radiation is X-ray radiation.

According to one embodiment, the display component comprises a bistable display media, and wherein a change in the electric potential at the respective pixel conductor relative to a drive voltage applied to the drive conductor changes the respective pixel area of the bistable display media from one stable display state to another stable display state.

According to one embodiment, the stack of layers further comprises one or more conductors capacitively coupled with the radiation-sensitive channels, wherein the degree of sensitivity of the radiation-sensitive channels can be tuned by applying one or more tuning voltages to the one or more conductors.

According to one embodiment, the stack of layers comprises one or more reflecting elements located between the radiation-sensitive channels and the display component for reflecting radiation back through the radiation-sensitive channels.

As discussed in more detail below, devices according to embodiments of the present invention require no external electronics outside of the stack to produce an image of the incident radiation.

There is also provided a method of displaying a visible image of a non-visible radiation pattern using a device as described above.

There is also provided a method of displaying a visible image of a non-visible radiation shadow using a device as described above.

There is also provided an apparatus comprising an X-ray source, and a device as described above.

There is also provided a method of imaging one or more internal parts of a human or animal body using an apparatus as described above.

Embodiments of the invention are described in detail hereunder, by way of example only, with reference to the accompanying drawings, in which.

Figure 1:
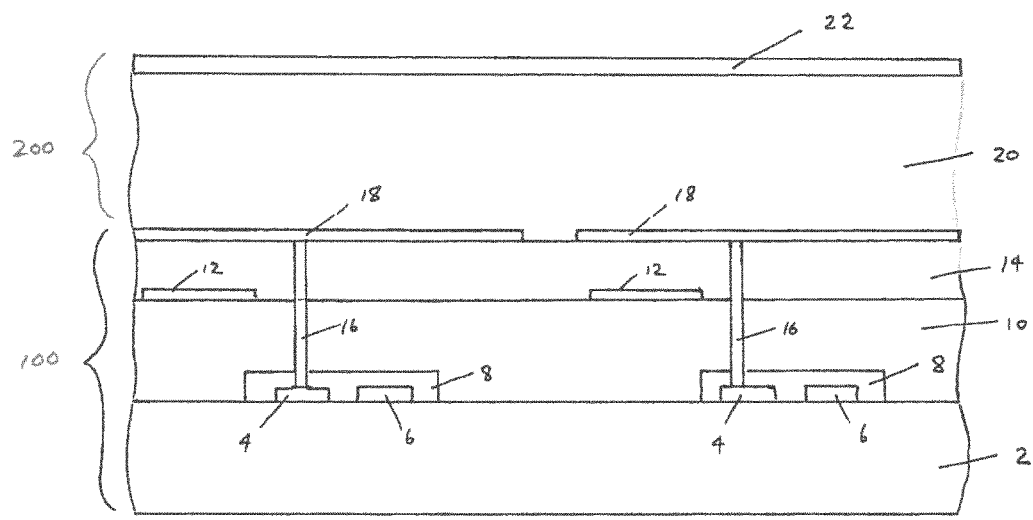
FIG. 1 illustrates an imaging device according to a first embodiment of the present invention.

With reference to FIG. 1, a radiation imaging device according to a first embodiment of the present invention includes the following elements. A first patterned conductor layer defining pairs of conductors 4, 6 is supported by a substrate 2 such as a glass substrate or a plastic substrate. Each pair of conductors comprises a drive conductor 6 which extends to the edge of the device for applying a drive voltage thereto, and a floating conductor 4 whose electric potential depends on the drive voltage applied to the drive conductor and the conductance of the semiconductor channel connecting the pair of conductors.

A planarisation layer (not shown) may be provided between the substrate 2 and the first patterned conductor layer. A patterned semiconductor layer 8 is formed over the first patterned conductor layer and defines a semiconductor channel between each pair of conductors 4, 6. A blanket insulator layer 10 is formed over the patterned semiconductor layer 8, to isolate COM conductor lines 12 from the semiconductor layer 8, which COM conductor lines 12 are defined by a second patterned conductor layer formed over the blanket insulator layer 10 and form pixel capacitors with the pixel conductors 18 mentioned later. A second blanket dielectric layer 14 is formed over the COM conductor lines 12 to prevent electrical shorting between the COM lines 12 and the pixel conductors 18 mentioned later. Via holes are formed in the insulator/dielectric layers 10, 14 down to each floating conductor 4. The via holes are filled with conductor material to create respective conductive connections 16 between each floating conductor 4 and the respective pixel conductor 18 mentioned later. A third patterned conductor layer is formed over the second blanket dielectric layer to define the pixel conductors 18. The pixel conductors 18 are thus connected to respective semiconductor channels wholly within the sequentially deposited stack of layers including the first patterned conductor layer, patterned semiconductor layer 8, insulator layer 10, and the second patterned conductor layer. The conductance of a semiconductor channel thus has a direct effect on the electric potential at the respective display pixel conductor 18, when a drive voltage is applied to the respective semiconductor channel via the drive conductor associated with that semiconductor channel.

The control component 100 thus formed is coupled to a display component 200 comprising a bistable optical media 20 and a common electrode 22 on the opposite side of the optical media 20 to the pixel conductors 18. Each pixel portion of the optical media 20 switches between two different stable optical states in response to a change in the potential difference between the electric potential at the respective pixel conductor and the electric potential at the common electrode 22. For the semiconductor channel material forming the semiconductor channels 8 between the floating and drive conductors 4, 6 is selected a semiconductor material whose conductance changes in dependence on the intensity of radiation to which it is exposed. A sufficiently large change in the intensity of the radiation to which a semiconductor channel 8 is exposed can lead to a change in the conductance of the semiconductor channel 8 (and consequently a change in the electric potential at the floating conductor 4 and pixel conductor 18 connected to the semiconductor channel 8 within the stack of layers) that is sufficiently large to cause the respective pixel portion of the optical media to switch from one stable optical state to the other stable optical state. One characteristic of a bistable optical media is that a switch to one stable optical state can be retained without requiring a continuation of the energy input required to trigger the switch to that state. In specific relation to the example described above, the switch to a different optical state triggered by the sufficiently large increase in radiation intensity can be retained even after the increase in radiation intensity ends, and even after the electric power source is disconnected from the drive conductors 6.

One example of a suitable bistable optical media is electrophoretic ink produced by E Ink Corporation. Those pixel portions of the optical media associated with semiconductor channels exposed to a radiation intensity below a threshold level may be in a "light" or "white" state, whilst those pixel portions of the optical media associated with semiconductor channels exposed to a radiation intensity above said threshold level are in a "dark" or "black" state, thereby creating a visible image providing information about the different levels of radiation intensity to which different areas of the device are exposed.

Another example of a bistable optical media is a cholesteric liquid crystal media.

Figure 2:
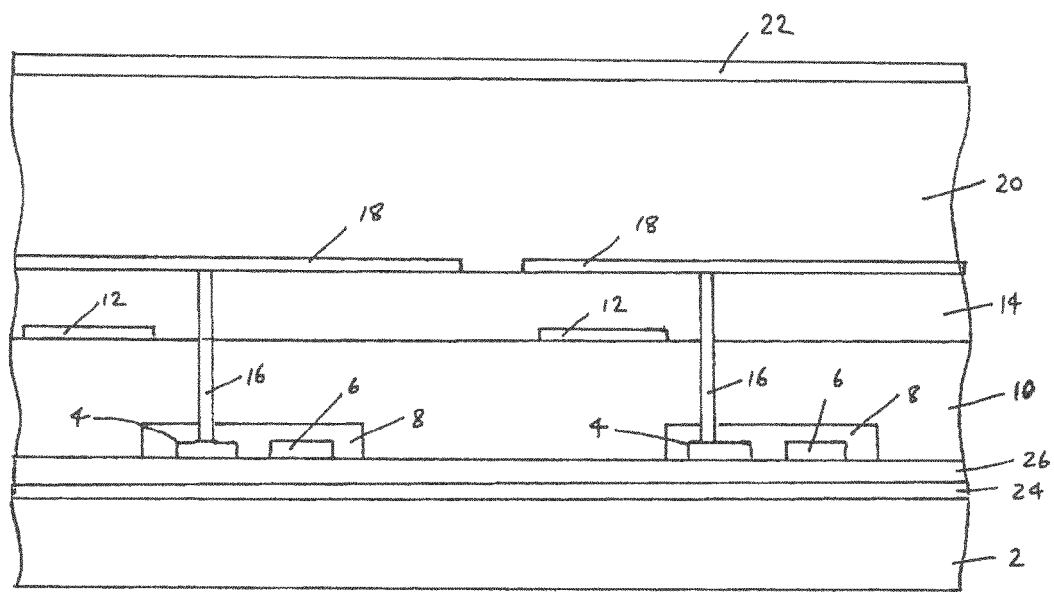
FIG. 2 illustrates an imaging device according to a second embodiment of the present invention.

The variation of FIG. 2 includes a scintillator 24 sandwiched between the substrate 2 and a planarisation layer 26. The scintillator 24 functions to generate a second type of radiation (e.g. visible light) in response to exposure to a first type of radiation (e.g. Xray radiation). The inclusion of the scintillator 24 is useful when, for example, the semiconductor channel material is sensitive to one type of radiation (e.g. visible radiation) but not to the type of radiation to be imaged (e.g, X-ray radiation). The scintillator 24 may generate many thousands of photons for each X-ray absorbed by the scintillator 24.

The speed at which each pixel portion can be switched between the two optical states, i.e. the sensitivity of the optical media 20 to radiation intensity changes via the semiconductor channels 8, can be increased using one or more of the following techniques. One technique involves controlling the drive voltage applied across the drive conductors and the common electrode 22 such that only a relatively small change in the conductance of the semiconductor channel 8 is required to trigger a switch of the optical media 20 from one stable optical state to the other. Another technique for the variation of FIG. 2 involves increasing the amount of the scintillator in the vicinity of each semiconductor channel such that even relatively small doses of radiation (e.g. X-ray radiation) generate sufficient photons to trigger a switch of the optical media 20 from one stable optical state to the other.

Another technique for increasing the sensitivity is to increase the semiconductor channel width, i.e. the width over which each pair of conductors are connected by the semiconductor. For example, the semiconductor channel length (i.e. the separation distance between the pair of conductors) could be e.g. 5 microns, and the semiconductor channel width could be hundreds or even thousands of microns. Large semiconductor channel widths can be achieved, for example, by using an interdigitated conductor arrangement where each pair of conductors is connected via the respective semiconductor channel.

Another technique for increasing the sensitivity is reducing the capacitance between the pixel electrodes 18 and the COM conductor lines 12. Reducing this pixel capacitance enables the necessary switching voltage to be achieved with less current. Capacitances of lower than 0.2 pF could be achieved by reducing the area of overlap between the COM lines 12 and the pixel electrodes 18. On the other hand, if sensitivity is less of a requirement, then larger capacitances between the pixel electrodes and the COM lines can be used to maintain the voltage across the media for longer periods. For example, a capacitance of 1 pF or higher could be used to maintain a switching voltage across the optical media for a few hundred milliseconds, which relatively high capacitances may be advantageous for devices including optical media for which switching of a pixel between two optical states best requires the switching voltage to be maintained at the pixel electrode for longer than the radiation exposure time. Relatively high capacitances may also be useful for deliberately reducing the sensitivity of the device to achieve better image contrast between pixels subject to different levels of radiation.

Another technique involves providing a reflecting element on the opposite side of each semiconductor channel 8 to the side from which the semiconductor channel 8 is exposed to radiation (i.e. on the opposite side of the semiconductor channel 8 to the scintillator 24 in the embodiment of FIG. 2). One example of such a technique involves providing the pixel electrodes 18 as reflecting metal elements, from which light is reflected back through the semiconductor channel 8 for the respective pixel thereby increasing the efficiency and reducing the size of the dose of radiation necessary to trigger a switch in the optical media.

Figure 3:
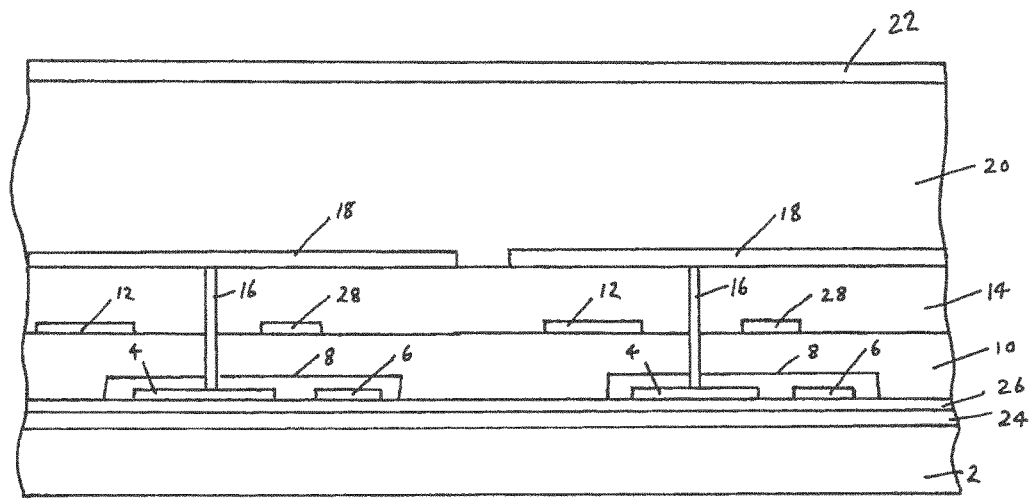
FIG. 3 illustrates an imaging device according to a third embodiment of the present invention.

FIG. 3 shows the provision of reflecting elements 28 at the same level as the COM conductor lines 12, which reflecting elements 28 are designed to reflect unabsorbed photons back through the semiconductor channel 8 for the respective pixel, thereby increasing the efficiency and reducing the size of the dose of radiation necessary to trigger a switch in the optical media. The reflecting elements 28 may comprise an array of reflecting metal lines, each line providing a reflective element for a respective row of pixels.

A common drive voltage is applied to all the drive conductors 6 relative to the common electrode 22 of the display component 200. The drive conductors 6 may comprise an array of parallel lines, each line providing the drive conductor 6 for a respective row of pixels, and extending to a common terminal at the lateral edge of the device.

Figure 4:
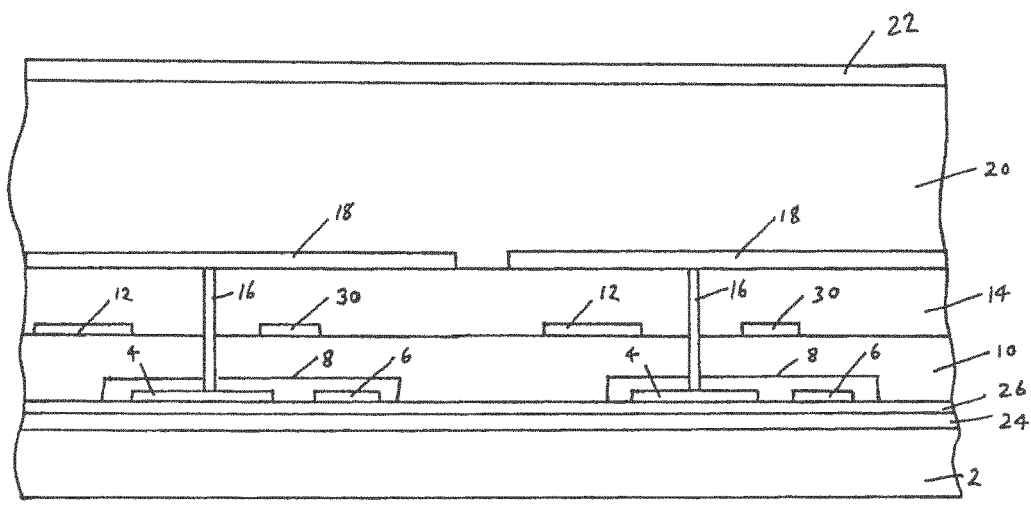
FIG. 4 illustrates an imaging device according to a fourth embodiment of the present invention.

The variation illustrated in FIG. 4 includes a further array of tuning conductor lines 30 at the same level as the COM conductor lines 12. The tuning conductor lines 30 can be used to tune the conductance of the semiconductor channels 8 in accordance with the desired degree of sensitivity for the imaging device. The tuning mechanism is a field-effect mechanism. For example, although each tuning conductor line 30 could be controlled independently, a more practical approach is to tune the conductance (and thereby adjust the threshold level of radiation intensity required to switch the optical media to a different optical state) of the whole of the semiconductor channels uniformly by applying a common tuning voltage to all tuning conductor lines 30. This tuning can be used, for example, for compensating for predictable changes in the semiconductor channel properties over time and/or compensating for the effect of changes in environmental conditions on the semiconductor channel properties. If these tuning conductor lines 12 are provided as reflecting metal elements, then these tuning conductor lines 30 can also function to reflect unabsorbed photons back through the semiconductor channel 8 for the respective pixel thereby increasing the efficiency and reducing the size of the dose of radiation necessary to trigger a switch in the optical media.

If the display component 200 itself and/or conductor components within the stack of layers of the control component 100 other does not sufficiently shield the semiconductor channels from ambient radiation incident on the display component 200, one or more radiation absorption layers could be included in the stack of layers. Similarly, for the above-described embodiment of providing a scintillator 24 on the opposite side of semiconductor channels 8 to the display component: if the scintillator itself does not sufficiently block the transmission of any radiation of the above-mentioned second type (e.g. visible radiation) incident on the substrate 2, the control component may further comprise e.g. between the substrate 2 and the scintillator a layer that absorbs/scatters/reflects radiation of the second type more than it does radiation of the first type (i.e. radiation to which the scintillator is sensitive).

Figure 5:
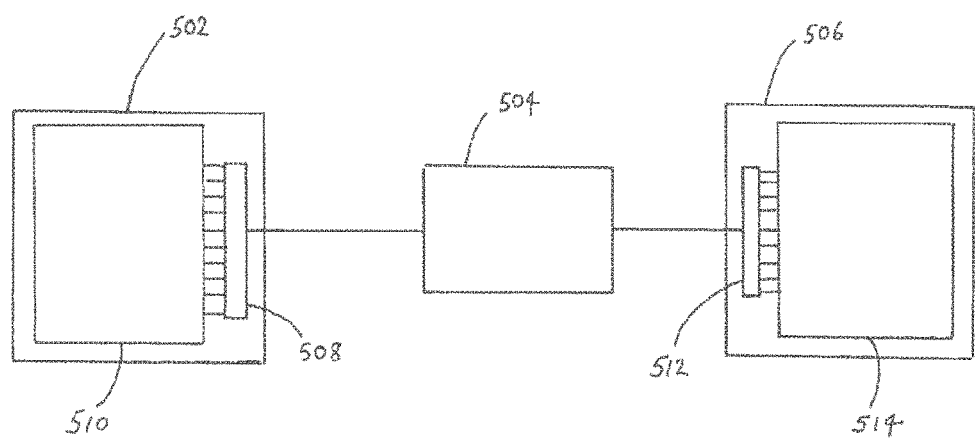
FIG. 5 schematically illustrates a conventional electronic sensor.

The above-described devices require no external electronics to produce the image; the devices can be operated simply by applying a battery voltage across a terminal connected to the drive conductors 6 and a terminal connected to the common electrode 22. This is in stark contrast to conventional electronic sensors, which, as schematically illustrated in FIG. 5) comprise a pixelated sensor array 502 which outputs signals to a processor 504, which in turn processes the signals received from the sensor array and outputs drive signals to a display device 506. For example, the pixelated sensor array 502 may comprise one or more driver chips 508 which convert electrical changes in the pixel sensor circuitry 510 to output signals for the processor 504; and the processor supplies drive signals to one or more driver chips 512 of the display device to control the generation of an image via an active matrix array of TFTs 514. Devices according to embodiments of the present invention produce images of incident radiation without using any driver chips or processor.

One example of a practical use for the above-described imaging devices is to provide a simple and robust X-ray sensor for medical purposes such as detecting bone fractures etc. For such use, the above-described sensitivity-adjusting techniques are used to provide a capability to generate an image with sufficiently high contrast from the relatively small sizes of X-ray doses used for patient diagnoses. X-ray sensors made from the above-described devices have the advantage that they offer instant feedback to the clinician, are easily portable, and can be reused. A record of the image can easily be made using a conventional digital camera or scanner.

The semiconductor channel material may be an organic or inorganic semiconductor material. The supporting substrate may, for example, be a glass substrate or a ore flexible substrate such as a plastic substrate.

In addition to any modifications explicitly mentioned above, it will be evident to a person skilled in the art that various other modifications of the described embodiments may be made within the scope of the invention.

The invention claimed is:

1. A device, comprising:
a display component; and
a drive component comprising a stack of layers defining an array of display pixel conductors each connected within the stack of layers to a drive conductor by a respective radiation-sensitive channel in electrical series between a pair of conductors of a patterned conductor layer,
wherein a change in the intensity of radiation to which a radiation-sensitive channel is exposed causes a change in a conductance of the radiation-sensitive channel and a change in the electric potential at the respective display pixel conductor relative to a drive voltage applied to the drive conductor, and
wherein the change in the electric potential at the respective display pixel conductor causes a change in the display of the respective pixel area of the display component.

2. A device according to claim 1, wherein the radiation is visible light.

3. A device according to claim 2, further comprising: a scintillator comprising a portion in the region of each radiation-sensitive channel, wherein respective portions of the scintillator generate a first type of radiation in the region of respective ones of the radiation-sensitive channels upon exposure to a second, different type of radiation.

4. A device according to claim 3, wherein said first type of radiation is visible light and/or ultraviolet radiation.

5. A device according to claim 3, wherein said second, different type of radiation is X-ray radiation.

6. A device according to claim 1, wherein the display component comprises a bistable display media, and wherein a change in the electric potential at the respective display pixel conductor relative to a drive voltage applied to the drive conductor changes the respective pixel area of the bistable display media from one stable display state to another stable display state.

7. A device according to claim 1, wherein the stack of layers further comprises one or more conductors capacitively coupled with the radiation-sensitive channels, wherein the degree of sensitivity of the radiation-sensitive channels can be tuned by applying one or more tuning voltages to the one or more conductors.

8. A device according to claim 1, wherein the stack of layers comprises one or more reflecting elements located between the radiation-sensitive channels and the display component for reflecting radiation back through the radiation-sensitive channels.

9. A device according to claim 1, wherein said pair of conductors of said patterned conductor layer comprises said drive conductor and a floating conductor.

10. A device according to claim 9, wherein said floating conductor has an electrical potential dependent on a drive voltage applied to the drive conductor and the conductance of the radiation sensitive channel.

11. A method comprising:
providing a device according to claim 1; and displaying a visible image of a non-visible radiation pattern using the device.

12. A method according to claim 11, comprising displaying said visible image while exposing the device to the non-visible radiation pattern.

13. A method according to claim 12, further comprising continuing to display said visible image after ending exposure of the device to the non-visible radiation pattern.

14. A method according to claim 12, further comprising continuing to display said visible image after disconnecting an electric power source to the drive conductor.

15. A method comprising:
   providing a device according to claim 1; and
   displaying a visible image of a non-visible radiation shadow using flail the device.

16. A method according to claim 15, comprising displaying said visible image while exposing the device to the non-visible radiation shadow.

17. A method according to claim 16, further comprising continuing to display said visible image after ending exposure of the device to the non-visible radiation shadow.

18. A method according to claim 16, further comprising continuing to display said visible image after disconnecting an electric power source to the drive conductor.

19. An apparatus comprising an X-ray source, and a device according to claim 5.

20. A method comprising:
   providing an apparatus according to claim 19; and
   imaging one or more internal parts of a human or animal body using the apparatus.

* * * * *